United States Patent
Shum et al.

(10) Patent No.: US 9,757,333 B2
(45) Date of Patent: Sep. 12, 2017

(54) STABILIZED ALL-AQUEOUS EMULSIONS AND METHODS OF MAKING AND USING THEREOF

(71) Applicant: Versitech Limited, Hong Kong (CN)

(72) Inventors: Ho Cheung Shum, Hong Kong (CN); Yang Song, Hong Kong (CN); Zhou Liu, Hong Kong (CN)

(73) Assignee: Versitech Limited, Hong Kong (HK)

( * ) Notice: Subject to any disclaimer, the term of this patent is extended or adjusted under 35 U.S.C. 154(b) by 0 days.

(21) Appl. No.: 14/564,365

(22) Filed: Dec. 9, 2014

(65) Prior Publication Data
US 2015/0157569 A1 Jun. 11, 2015

Related U.S. Application Data

(60) Provisional application No. 61/913,653, filed on Dec. 9, 2013.

(51) Int. Cl.
*A61K 9/107* (2006.01)
*A61K 47/10* (2017.01)
*A61K 47/36* (2006.01)
*B01F 5/00* (2006.01)
*B01F 3/08* (2006.01)
*B01F 17/00* (2006.01)
*A61K 9/00* (2006.01)

(52) U.S. Cl.
CPC .............. *A61K 9/107* (2013.01); *A61K 47/10* (2013.01); *A61K 47/36* (2013.01); *B01F 3/0803* (2013.01); *B01F 3/0815* (2013.01); *B01F 5/0085* (2013.01); *A61K 9/0019* (2013.01); *A61K 9/0095* (2013.01); *B01F 17/0092* (2013.01)

(58) Field of Classification Search
CPC ........ A61K 9/107; A61K 47/36; A61K 47/10; A61J 3/00; B01F 17/0092
USPC .................... 424/9.1, 400, 93.1; 514/777, 76
See application file for complete search history.

(56) References Cited

U.S. PATENT DOCUMENTS

2007/0113530 A1* 5/2007 Morozov ........... B01D 39/1623
55/527

OTHER PUBLICATIONS

Andes-Koback and Keating, "Complete budding and asymmetric division of primitive model cells to produce daughter vesicles with different interior and membrane compositions", J. Am. Chem. Soc. 133:9545-9555 (2011).
Balakrishnan, et al., "Particles trapped at the droplet interface in water-in-water water emulsions", Langmuir 28:5921-26 (2012).
Boreyko, at al., "Aqueous two-phase microdroplets with reversible phase transitions", Lab Chip 13:1295-1301 (2013).
Bransky, et al., "A microfluidic droplet generator based on a piezoelectric actuator", Lab Chip 9:516-20 (2009).
Brunette and Till, "A rapid method for the isolation of L-cell surface membranes using an aqueous two-phase polymer system", J. Membr. Biol. 5:215-24 (1971).
Cans, at al., "Positioning lipid membrane domains in giant vesicles by micro-organization of aqueous cytoplasm mimic", J. Am. Chem. Soc. 130:7400-6 (2008).
Chen, et al., "One-step multicomponent encapsulation by compound-fluidic electrospray", J. Am. Chem. Soc. 130:7800-01 (2008).
Deng, at al., "Increase of electrospray throughput using multiplexed microfabricated sources for the scalable generation of monodisperse droplets", J. Aerosol Sci., 37:696-714 (2006).
Diamond and Hsu, "Aqueous two-phase systems for biomolecule separation", Adv. Biochem. Eng. Biotechnol. 47:89-135 (1992).
Diamond and Hsu, Phase diagrams for dextran-PEG aqueous two-phase systems at 22°C, Biotechnol. Tech., 3:119-24 (1989).
Diamond and Hsu, "Protein partitioning in PEG/dextran aqueous two-phase systems", AIChE J. 36:1017-24 (1990).
Ding, et al., "Interfacial tension in phase-separated gelatin/dextran aqueous mixtures", Colloid Interface Sci.,253:367-76 (2002).
Eggers and Villermaux, "Physics of liquid jets", Rep. Prog. Phys. 71, 036601 (2008).
Forciniti, et al., "Interfacial tension of polyethyleneglycol-dextran-water systems: influence of temperature and polymer molecular weight", J. Biotechnol. 16:279-96 (1990).
Geschiere, et al., "Slow growth of the Rayleigh-Plateau instability in aqueous two phase systems", Biomicrofluidics 6, 022007 (2012).
Giraldo-Zuniga, et al., "Interfacial Tension and Viscosity for Poly-(ethylene glycol) + Maltodextrin Aqueous Two-Phase Systems", J. Chem. Eng. Data 51:1144-7 (2006).
Haas, "Formation of Uniform Liquid-Drops by Application of Vibration to Laminar Jets", Ind. Eng. Chem. Res., 31:959-67 (1992).
Hatti-Kaul, "Aqueous two-phase systems. A general overview", Mol. Biotechnol. 19:269-77 (2001).

(Continued)

*Primary Examiner* — Robert Cabral
(74) *Attorney, Agent, or Firm* — Pabst Patent Group LLP

(57) ABSTRACT

Methods for preparing all-aqueous emulsions, including stable emulsions or emulsions having high viscosity and/or ultra-low interfacial tension are described. The method includes mixing, combining, or contacting a first electrically charged phase containing a first solute (e.g., dispersed phase) with at least a second phase containing a second solute (e.g., continuous phase). The solutes are incompatible with each other. The electrostatic forces between the two phases induce the formation of droplets of a dispersed phase in a continuous phase. The dispersed and continuous phases contain oppositely charged molecules, such as surfactants or other macromolecules and colloids which stabilize the drops of the dispersed phase. Complex coacervation of the oppositely charged molecules or colloids at the interface of the two aqueous phases results in formation of a membrane or barrier which prevents coalescence or aggregation of the droplets. The membrane also prevents leakage of any encapsulated agents from the droplets.

17 Claims, 1 Drawing Sheet

(56) References Cited

OTHER PUBLICATIONS

Hong, et al., "PEGylated polyethylenimine for in vivo local gene delivery based on lipiodolized emulsion system", J. Controlled Release 99:167-76 (2004).

Jaworek, "Electrostatic micro- and nanoencapsulation and electroemulsification: a brief review", J. Microencapsulation 25:443-68 (2008).

Kaneda, et al., "Perfluorocarbon nanoemulsions for quantitative molecular imaging and targeted therapeutics", Ann. Biomed. Eng. 37:1922-33 (2009).

Keating, "Aqueous phase separation as a possible route to compartmentalization of biological molecules", Acc. Chem. Res. 45:2114-24 (2012).

Kim, et al., "Multiple polymersomes for programmed release of multiple components", J. Am. Chem. Soc. 133:15165-71 (2011).

King, et al., "Molecular thermodynamics of aqueous two-phase systems for bioseparations", AIChE J. 34:1585-94 (1988).

Lai, et al., "Rounded multi-level microchannels with orifices made in one exposure enable aqueous two-phase system droplet microfluidics", Lab on a Chip, 20:3551 (2011).

Lee, et al., "Microfluidic mixing: a review", Int. J. Mol. Sci., 12:3263-87 (2011).

Lee, et al., "Where physics meets chemistry meets biology for fundamental soft matter research.", Soft Matter 8:3924-3928 (2012).

Li, et al., "Preparation and characterization of crosslinked starch microspheres using a two-stage water-in-water emulsion method", Carbohydr. Polym. 88:912-916 (2012).

Long, et al., "Dynamic microcompartmentation in synthetic cells", PNAS, 102:5920-5925 (2005).

Lorenzen, "Effects of time/temperature-conditions of pre-heating and enzymatic cross-linking on thermo-functional properties of reconstituted dairy ingredients", Food Res. Int., 40:700-8 (2007).

Lu, et al., "Phase separation of parallel laminar flow for aqueous two phase systems in branched microchannel", Microfluid Nanofluid 10:1079-1086 (2011).

Ma, et al., Cell Delivery: Core-Shell Hydrogel Microcapsules for Improved Islets Encapsulation, Adv. Healthcare Mater. 2:768 (2013).

Nguyen, et al., "Stabilization of water-in-water emulsions by addition of protein particles", Langmuir 29:10658-10664 (2013).

Pojman, et al., "Evidence for the existence of an effective interfacial tension between miscible fluids: isobutyric acid-water and 1-butanol-water in a spinning-drop tensiometer.", Langmuir 22:2569-2577 (2006).

Rossow, et al., "Controlled synthesis of cell-laden microgels by radical-free gelation in droplet microfluidics", J. Am. Soc. 134:4983-4989 (2012).

Sauret, et al., "Fluctuation-induced dynamics of multiphase liquid jets with ultra-low low interfacial tension", Lab Chip 12:3380-6 (2012b).

Sauret and Shum, "Forced generation of simple and double emulsions in all-aqueous aqueous systems", Appl. Phys. Lett. 100:154106 (2012a).

Simeone, et al., "Phase diagram, rheology and interfacial tension of aqueous mixtures of Na-caseinate and Na-alginate", Food Hydrocolloids 18:463-470 (2004).

Simon, et al., "Water-in-water emulsions stabilized by non-amphiphilic interactions: polymer-dispersed lyotropic liquid crystals",Langmuir 23:1453-1458 (2007).

Song, et al., "All-aqueous multiphase microfluidics", Biomicrofluidics,7:061301 (2013b).

Song, et al., "Manipulation of viscous all-aqueous jets by electrical charging", Chem. Commun. 49:1726-1728 (2013a).

Song, et al., "Microextraction in a tetrabutylammonium bromide/ammonium sulfate aqueous two-phase system and electrohydrodynamic generation of a micro-droplet", J. Chromatogr, A 1162:180-186 (2007).

Song and Shum, "Monodisperse w/w/w double emulsion induced by phase separation", Langmuir 28:12054-12059 (2012).

Su and Chiang, "Partitioning and purification of lysozyme from chicken egg white using aqueous two-phase system", Process Biochem. 41:257-263 (2006).

Tang and Gomez, "Generation by electrospray of monodisperse water droplets for targeted drug delivery by inhalation", J. Aerosol Sci. 25:1237-1249 (1994).

Wu, et al., "Fabrication and characterization of monodisperse PLGA-alginate core-shell microspheres with monodisperse size and homogeneous shells for controlled drug release" Acta Biomater. 9:7410-9 (2013).

Wu, et al., "Interfacial Tension of Poly(ethylene glycol) + Salt + Water Systems", J. Chem, Eng. Data 41:1032-1035 (1996).

Zhang, et al., "Polymersomes of asymmetric bilayer membrane formed by phase-guided assembly", J. Controlled Release 147:413-419 (2010).

Zhao, et al., "Plasma lysophosphatidylcholine levels: potential biomarkers for colorectal cancer", Adv. Mater. 19:2696-2701 (2007).

Ziemecka, et al., "Monodisperse hydrogel microspheres by forced droplet formation in aqueous two-phase systems", Lab Chip, 11:620-4 (2011a).

Ziemecka, et al., "Where physics meets chemistry meets biology for fundamental soft matter research", Soft Matter 7:9878-9880 (2011b).

Zoltowski, et al., "Evidence for the existence of an effective interfacial tension between miscible fluids. 2. Dodecyl acrylate-poly(dodecyl acrylate) in a spinning drop tensiometer", Langmuir, 23:5522-5531 (2007).

* cited by examiner

STABILIZED ALL-AQUEOUS EMULSIONS AND METHODS OF MAKING AND USING THEREOF

CROSS-REFERENCE TO RELATED APPLICATIONS

This application claims benefit of U.S. Provisional Application No. 61/913,653, filed Dec. 9, 2013. Application No. 61/913,653, filed Dec. 9, 2013, is hereby incorporated herein by reference in its entirety.

FIELD OF THE INVENTION

This invention is in the field of all-aqueous emulsions, particularly stabilized all-aqueous emulsions.

BACKGROUND OF THE INVENTION

Aqueous two-phase systems (ATPSs), or all-aqueous emulsions, are formed by dissolving two incompatible solutes in water above the critical concentrations for phase separation. These incompatible solutes can redistribute in water and form immiscible aqueous phases, if the reduction in enthalpy is sufficient to overcome the energy cost associated with the increased entropy. This often requires each solute species of an ATPS to interact more strongly with itself than with the other species, leading to the segregation of solute of the same species and phase separation. However, the segregation is incomplete and each phase usually still contains a small amount of molecules of the other species.

For example, in the equilibrium phase diagram of the PEG/dextran/$H_2O$ system, the dextran-rich phase contains a minute amount of PEG; similarly, the PEG-rich phase also contains dextran. Compositions of equilibrium phases vary with the molecular weight of incompatible solutes, temperature and other salt additives. The incomplete separation leads to lower mixing entropy than a complete separation, and thus reduces the energetic cost of phase separation.

Immiscible phases formed by the phase separation of ATPSs are free of organic solvents; thus they are biocompatible and eco-friendly in biomedical research studies and applications. In the synthesis of biomaterials, such as protein microspheres and hydrogel beads, organic solvents are usually involved. Upon solidifying the dispersed phase to form solid materials, organic solvents must be extracted by repeated washing. These tedious steps to remove the organic phases can be avoided when ATPSs are used to form emulsions. Moreover, when protein solutions are exposed to the oil phases, denaturation of proteins often occurs at the water-oil (w/o) interface, reducing the bioactivity of the proteins. The use of ATPS can avoid the detrimental effects of organic solvents to the bioactivity of proteins and the viability of cells.

Traditional methods for fabricating all-aqueous emulsions, such as vortex mixing and homogenization, do not allow for control of the sizes and/or structures of the resultant all-aqueous emulsions. To overcome these limitations, microfluidics has been investigated for the preparation of all-aqueous emulsions. While microfluidic devices enable the generation of water-in-oil (w/o) or oil-in-water (o/w) emulsions with high monodispersity and control over droplet shapes and structures, formation of monodisperse w/w emulsion is not easily achieved in typical microfluidic channels owing to the low interfacial tension of such systems. Breakup of the jet in the low interfacial tension systems usually results in polydisperse droplets because of the large Capillary and Weber numbers.

Attempts to overcome the limitations of microfluidic approaches have been explored. For example, perturbation has been investigated as a means for producing all aqueous emulsions. To induce the breakup of a w/w jet, a vibration source is introduced in the system to generate initial corrugations on the surface of a w/w jet. These vibrations can be incorporated into the microfluidic devices by embedding a piezoelectric actuator in the channel wall or by using a mechanical vibrator that squeezes the soft tubing connected to the incoming channel. The vibrator imposes fluctuations to the driving pressure and modulates the instantaneous flow rate of the perturbed phase, changing locally the diameters of the w/w jet. The shape of the corrugated jet can be controlled by applying appropriate frequency and amplitude of perturbation.

However, the perturbation approach has not been demonstrated in all-aqueous systems with dynamic viscosity of 100 mPa·s or above. An efficient breakup of a viscous w/w jet is restricted by the low growth rate of the Rayleigh-Plateau instability. Moreover, emulsions prepared using this approach are only stable for short periods of time due to coalescence of the dispersed phase.

There exists a need for methods of producing stable all-aqueous emulsions with high monodispersity, particularly emulsions with high viscosity (e.g., ≥100 mPa·s) and/or ultra-low interfacial tension.

Therefore, it is an object of the invention to provide methods of producing stable all-aqueous emulsions with high monodispersity, particularly emulsions with high viscosity (e.g., ≥100 mPa·s) and/or ultra-low interfacial tension.

SUMMARY OF THE INVENTION

Methods for preparing all-aqueous emulsions, including stable emulsions and/or emulsions having high viscosity and/or ultra-low interfacial tension are described herein. The method includes mixing, combining, or contacting a first electrically charged phase containing a first solute (e.g., dispersed phase) with at least a second phase containing a second solute (e.g., continuous phase). The solutes are incompatible with each other. The electrostatic forces between the two phases induce the formation of droplets of a dispersed phase in a continuous phase.

The dispersed and continuous phases contain oppositely charged molecules and colloids, such as surfactants, macromolecules, nanoparticles, or nanofibers, which stabilize the drops of the dispersed phase. Complex coacervation of the oppositely charged molecules or colloids at the interface of the two aqueous phases results in formation of a membrane or barrier which prevents coalescence or aggregation of the droplets. The membrane also prevents leakage of any encapsulated agents (e.g., therapeutic, prophylactic, and/or diagnostic agents) from the droplets.

The emulsions described herein can be used for a variety of applications, such as drug delivery (e.g., small molecules, biomolecules, cells, etc.), materials fabrications, modeling of biological organelles, encapsulation of flavorings, dyes, vitamins, etc. for food and beverage applications; encapsulation of actives for cosmetics; encapsulation of growth factors, stem cells or other biomolecules for biomedical applications; encapsulation of chemical reactants for chemical reactions, and combinations thereof.

DETAILED DESCRIPTION OF THE INVENTION

I. Definitions

Figure 1:
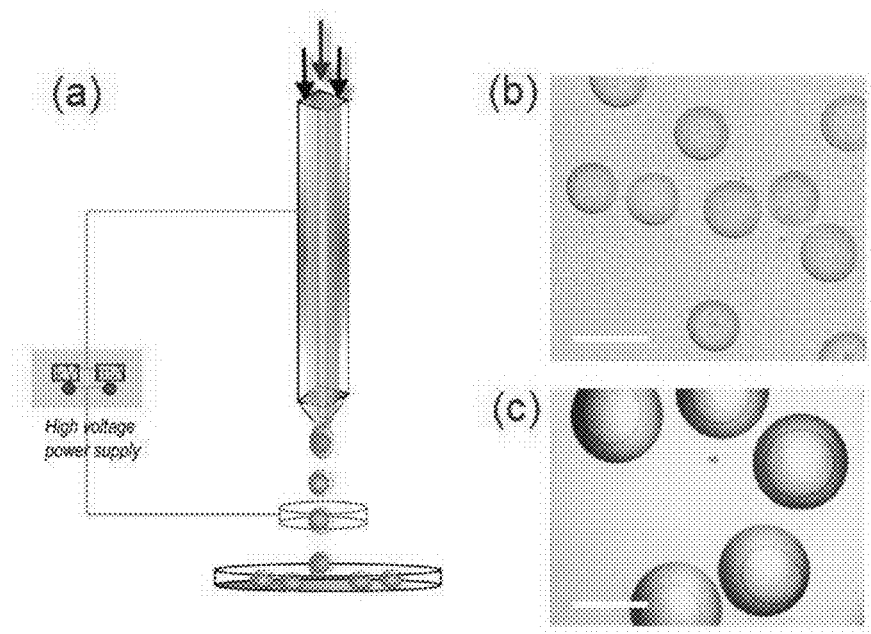
FIG. 1 shows formation of aqueous droplets. Panel a is a schematic of the formation of aqueous droplets in the all-aqueous electrospray approach. Panel b is optical microscopic images of monodisperse aqueous droplets produced by all-aqueous electrospray. Panel c is microscopic images of all-aqueous emulsions with a core-shell structure. Droplets are collected on a glass slide. Scale bar is 200 µm.

"All-aqueous emulsion" and "Aqueous two-phase systems (ATPSs)" are used interchangeable and refer to an emulsion containing an aqueous dispersed phase in an aqueous continuous phase.

"Ultra-low interfacial tension", as used herein, generally means the interfacial tension between the two aqueous phases are less than 2 mN/m "Stable," as used herein, generally means that the dispersed phase remains separated rather than fusing into a continuous liquid phase over an extended period of time.

"Incompatible," as used herein, generally means the binding energy between two solute molecules of the same kind is lower than the binding energy between two different kinds of solute molecules.

II. Electrostatic Methods for Producing all Aqueous Emulsions

Methods for preparing all-aqueous emulsions, including stable emulsions and/or emulsions having high viscosity and/or ultra-low interfacial tension are described herein. The method includes mixing, combining, or contacting a first electrically charged phase containing a first solute (e.g., first phase) with at least a second phase containing a second solute (e.g., continuous phase). In some embodiments, only one solution is charged, although the both solutions may be charged. The solutes are incompatible with each other. It has been discovered that the electrostatic forces between the two solutions induce the formation of droplets of a dispersed phase in a continuous phase.

The dispersed and continuous phases contain oppositely charged molecules and colloids, such as surfactants, macromolecules, nanoparticles, or nanofibers, such as surfactants or other macromolecules, which stabilize the drops of the dispersed phase. Complex coacervation of the oppositely charged molecules or colloids at the interface of the two aqueous phases results in formation of a membrane or barrier which prevents coalescence or aggregation of the droplets. The membrane also prevents leakage of any encapsulated agents (e.g., therapeutic, prophylactic, and/or diagnostic agents) from the droplets.

A. Incompatible Solutes

Aqueous two-phase systems (ATPSs) are formed by dissolving two incompatible solutes in water above the critical concentrations for phase separation. These incompatible solutes can redistribute in water and form immiscible aqueous phases, if the reduction in enthalpy is sufficient to overcome the energy cost associated with the increased entropy. This often requires each solute species of an ATPS to interact more strongly with itself than with the other species, leading to the segregation of solute of the same species and phase separation.

A variety of solutes known in the art can be used to form the all-aqueous emulsions. Exemplary solutes include, but are not limited to, polymers, such as polyethylene glycol (PEG), dextran, methyl cellulose, sodium dextran sulfate, polyvinyl alcohol (PVA), and polyvinyl pyrrolidone (PVP), caseinate, and alginate; salts, such as phosphates (e.g., tripotassium phosphate and disodium phosphate), citrates (e.g., sodium citrate), sulfates (e.g., sodium sulfate), and carbonates. In some embodiments, one phase contains PEG and the other phase contains dextran.

The concentration of the solute can vary depending on the nature of the solutes. Generally, the concentration is from about 3.5 wt % to the solubility limited in water. In those embodiments where the solutes are PEG and dextran, the concentration of PEG is from about 3.5 wt % to about 20 wt % and the concentration of dextran is from about 3.5 wt % to the solubility limit of dextran.

The weight average molecular weight of PEG is from about 1,000 Daltons to about 100,000 Daltons, preferably about 2,000 Daltons to about 20,000 Daltons, preferably from about 2,000 Daltons to about 10,000 Daltons, more preferably from about 5,000 Daltons to about 10,000 Daltons. In some embodiments, the molecular weight of PEG is about 8,000 Daltons.

The weight average molecular weight of dextran is from about 40,000 Daltons to about 1,000,000 Daltons, preferably about 70,000 Daltons to about 500,000 Daltons. In some embodiments, the molecular weight is about 500,000 Daltons.

B. Therapeutic, Prophylactic, and Diagnostic Agents

One or more phases can contain one or more therapeutic, prophylactic, and/or diagnostic agents. In some embodiments, the solution that forms the dispersed phase contains one or more therapeutic, prophylactic, and/or diagnostic agents which are encapsulated within the droplets upon formation of the emulsion. In the methods described herein, the solutions can contain surfactants which are charged oppositely to the charge of the solution to which it is added. Coacervation of the charged surfactants at the interface of the incompatible solutions results in the formation of a membrane which can prevent leakage of encapsulated agents.

The one or more therapeutic, prophylactic, and/or diagnostic agents can be small molecule therapeutic agents (e.g., agents having molecular weight less than 2000 amu, 1500 amu, 1000, amu, 750 amu, or 500 amu) and/or biomolecules, such as a proteins, nucleic acids (e.g., DNA, RNA, siRNA, etc.), enzymes, etc.; and/or cells.

In some embodiments, the agent is a biomolecule, such as a protein, enzyme, nucleic acid, etc. Biomolecules can be denatured in the presence of an organic solvent. Therefore, all aqueous emulsions provide a vehicle for delivering such agents while preserving the biological activity of the agent.

Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are drugs and imaging agents. Therapeutic agents include antibiotics, antivirals (especially protease inhibitors alone or in combination with nucleosides for treatment of HIV or Hepatitis B or C), anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs, antisense, aptamers, ribozymes, external guide sequences for ribonuclease P, and triplex forming agents).

Particularly preferred drugs to be delivered include anti-angiogenic agents, antiproliferative and chemotherapeutic agents such as rampamycin.

Exemplary diagnostic materials include paramagnetic molecules, fluorescent compounds, magnetic molecules, and radionuclides.

Peptide, protein, and DNA based vaccines may be used to induce immunity to various diseases or conditions. For example, sexually transmitted diseases and unwanted pregnancy are world-wide problems affecting the health and welfare of women. Effective vaccines to induce specific immunity within the female genital tract could greatly reduce the risk of STDs, while vaccines that provoke anti-sperm antibodies would function as immunocontraceptives. Extensive studies have demonstrated that vaccination at a distal site—orally, nasally, or rectally, for example—can induce mucosal immunity within the female genital tract. Of these options, oral administration has gained the most interest because of its potential for patient compliance, easy administration and suitability for widespread use. Oral vaccination with proteins is possible, but is usually inefficient or requires very high doses. Oral vaccination with DNA, while potentially effective at lower doses, has been ineffective in most cases because 'naked DNA' is susceptible to both the stomach acidity and digestive enzymes in the gastrointestinal tract.

C. Cells

The emulsions described herein are prepared from an aqueous dispersed phase and an aqueous continuous phase and therefore do not contain any organic solvents. Such emulsions are desirable for encapsulating cells, the viability of which can be adversely affected by the organic solvents. The cells can be added to the solution that becomes the dispersed phase and/or the solution that becomes the continuous phase.

Exemplary cell types include, but are not limited to, kerotinocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, stem or progenitor cells, neurobalstoma, chondrocytes, skin cells and bone-forming cells.

D. Emulsion Stabilization

Although the all-aqueous emulsions with controlled and tunable structures have been generated with different approaches, all of these emulsions are only transiently stable and tend to coalesce subsequently. Stabilization of these emulsions is thus useful in both scientific studies and practical applications.

1. All-Aqueous Emulsion Templated Materials

Stabilized emulsion structures can be produced by selectively solidifying the dispersed phases, forming hydrogel beads or capsules. To prevent the coalescence of droplets, photo-curable monomers such as PEGDA or dextran-HEMA can be added to the emulsion phase, and the fast photo-polymerization helps to solidify the emulsion within seconds. However, photo-polymerization typically generates toxic free radicals, potentially harming the encapsulated species, especially the living ones. To achieve radical-free gelation, the emulsion phase can be solidified by diffusing biocompatible cross-linkers to the gel precursors in the emulsion phase. For example, when a sodium alginate solution is used as the emulsion phase, the emulsion can be quickly solidified within a minute by introducing calcium ions. Leakage of encapsulated species is negligible within the time scale of emulsion gelation. Nevertheless, many biocompatible gelation reactions, such as enzyme-induced gelation, last for hours to days, where leakage of encapsulated species cannot be disregarded. In this manner, a compact membrane must quickly form at the w/w interface, preventing the leakage of encapsulated species.

2. Water/Water Interface-Templated Materials

In other embodiments, the emulsion can be stabilized by forming a membrane or barrier on the surface of the dispersed phase droplets to prevent coalescence. Aggregation of particles or macromolecular surfactants at the w/w interface is the primary mechanism of emulsion destabilization. Submicron-sized latex microspheres and protein particles can be irreversibly trapped at the w/w interface. This feature indicates that the absorption energy is larger than the kinetic energy imposed by thermal activation. With a sufficiently large concentration of protein particles and high w/w interfacial tension, protein particles successfully stabilize the PEG/dextran emulsion for a few weeks. However, in the presence of a shear flow, these particles detach from the w/w interface and fail to stabilize the emulsion. Strengthening the binding force among the protein particles may prevent the detachment from the interfaces induced by the shear flow. Enhancement of the binding force can be realized through the addition of cross-linkers, such as glutaraldehyde, polyethyleneimine, sodium dextran sulfate, polysaccharide, etc.; or through thermal incubation to induce the gelation of protein particles.

Self-assembly of macromolecules at the w/w interface provides another possible solution to stabilize the all-aqueous emulsions. To form stable emulsions, macromolecular surfactants should aggregate at the w/w interface and form a compact membrane. Aggregation of the surfactants at the w/w interface is strongly affected by their interactions with the dissolved solutes in aqueous phases. The presence of such interaction is confirmed by the observation of budding of liposomes encapsulating two immiscible aqueous phases. In this example, two aqueous phases selectively approach the different lipid domains after extraction of water from the liposomes. The interaction between the membrane and the incompatible solutes also keeps the membrane at the w/w interface. This hypothesis is confirmed by using copolymers to form vesicles from the templates of w/w emulsions. In this study, the copolymers of the PEG-polycaprolactone (PCL) and the dextran-PCL are separately added into the PEG-rich and the dextran-rich phase. Upon vortex mixing of the two phases, the two copolymers spontaneously aggregate at the w/w interface. More importantly, the PCL moieties facilitate the formation of a compact membrane, probably due to the hydrophobic interactions.

i. Charged Surfactants/Lipids

The dispersed phase and the continuous phase can contain one or more surfactants and/or lipids that are oppositely charged. Upon contacting the two solutions, the oppositely charged surfactants undergo complex coacervation of the surfactants at the interface of the two aqueous phases resulting in formation of a membrane or barrier which prevents coalescence or aggregation of the droplets. The membrane also prevents leakage of any encapsulated agents (e.g., therapeutic, prophylactic, and/or diagnostic agents) from the droplets.

Suitable charged surfactants include cationic surfactants and anionic surfactants. Anionic surfactants typically contain one or more negatively charged groups or groups, such as sulfate, sulfonate, phosphate, and carboxylates. Exemplary anionic surfactants include, but are not limited to, alkyl sulfates, such as ammonium lauryl sulfate, sodium lauryl sulfate (SDS, sodium dodecyl sulfate) and the related alkyl-ether sulfates sodium laureth sulfate, also known as sodium lauryl ether sulfate (SLES), and sodium myreth sulfate; docusates, such as dioctyl sodium sulfosuccinate, perfluorooctanesulfonate (PFOS), perfluorobutanesulfonate, linear alkylbenzene sulfonates (LABs), alkyl-aryl ether phosphates and the alkyl ether phosphates, and carboxylates, such as alkyl carboxylates (soaps), including sodium stearate. Other examples include sodium lauroyl sarcosinate and carboxylate-based fluorosurfactants such as perfluorononanoate, perfluorooctanoate (PFOA or PFO).

Cationic surfactants typically contain one or more positively charged groups or head groups, such as pH-dependent primary, secondary, or tertiary amines and permanently charged quaternary ammonium cations. Exemplary cationic surfactants include, but are not limited to, alkyltrimethylammonium salts, such as cetyl trimethylammonium bromide (CTAB) and cetyl trimethylammonium chloride (CTAC), cetylpyridinium chloride (CPC), benzalkonium chloride (BAC), benzethonium chloride (BZT), 5-bromo-5-nitro-1,3-dioxane, dimethyldioctadecylammonium chloride, cetrimonium bromide, and dioctadecyldimethylammonium bromide (DODAB).

Other charged molecules include, but are not limited to, lipids (e.g., phospholipids, sphingolipids, skin lipids, etc.), amphiphilic block copolymers, polyelectrolytes, and combinations thereof.

The concentration of the oppositely charged materials is generally close to the critical micelle concentration, for example, from about 0.1 wt % to about 1.0 wt %. However, the concentration can vary for a given charged molecule.

E. Techniques for Manufacture

Techniques known in the art can be used to prepare the stabilized emulsions described herein. In some embodiments, the emulsion is prepared using an electrospray technique.

Electrospray is a method of generating a very fine liquid aerosol through electrostatic charging. In electrospray, a liquid is passing through a nozzle. The plume of droplets is generated by electrically charging the liquid to a very high voltage. The charged liquid in the nozzle becomes unstable as it is forced to hold more and more charge. Soon the liquid reaches a critical point, at which it can hold no more electrical charge and at the tip of the nozzle it blows apart into a cloud of tiny, highly charged droplets. These tiny droplets are typically less than 10 µm in diameter and fly about searching for a potential surface to land on that is opposite in charge to their own. As the droplets fly about, they rapidly shrink as solvent molecules evaporate from their surface. Since it is difficult for charge to evaporate, the distance between electrical charges in the droplet dramatically decreases. If the droplet can't find a surface in which to dissipate its charge in time, the electrical charge reaches a critical state and the droplet will violently blow apart again.

In the methods described herein, electrospray is used to contact a first aqueous solution containing a first solute and a second aqueous solution containing a second solute, wherein the solutes are incompatible. One of the solutions becomes the dispersed phase in the emulsion while the other becomes the continuous phase. The dispersed and continuous aqueous phase(s) are separated by a middle phase of air, preventing the mixing of charged solutes induced by high voltage. In some embodiments, a dispersed phase (e.g., PEG-containing solution) is charged with a high DC voltage and is sprayed into an immiscible aqueous solution containing the second solute (e.g., dextran) through air. The large surface tension between the dispersed phase and air helps to break up the jet quickly into droplets. A dripping to jetting transition is observed upon an increase in the applied voltage. In the dripping regime, the charged jet immediately breaks up at the end of the spraying nozzle, yielding monodisperse droplets with a polydispersity of less than 5%, 4%, 3%, 2%, or 1%. In the jetting regime, droplets with a polydispersity typically higher than those formed in the dripping regime are formed at the end of the Taylor cone. A reduction in the size of the spraying nozzle reduces the diameter of the jet, thus facilitating the fast formation of droplets in the electro-dripping regime.

The diameters of the dispersed droplets can be varied as a function of the applied voltage. For example, the diameter of PEG-droplets dispersed in a dextra continuous phase varied from about 800 microns to about 120 microns by increasing the strength of the electric field from 1.0 kV/cm to 8.0 kV/cm. At these voltages, the droplets were monodisperse. Polydisperse droplets are obtained with further increases in the applied voltage.

A core-shell structured emulsion can also be generated with the all-aqueous electrospray approach. A round capillary with a tapered nozzle can be coaxially inserted into another tapered squared capillary, forming a co-flowing geometry. Two immiscible aqueous phases are separately injected into the inner and outer glass capillaries, forming an inner phase-in-outer phase jet. The outer phase can be charged by a high-voltage power supply and the compound jet is forced to go through a ring-shaped counter electrode under electrostatic forces. Upon breakup of the jet, core-shell structured droplets finally fall into the continuous phase. The relative sizes of the core and shell of the emulsion can be easily adjusted by changing the flow rates ratios of the two fluids. For example, varying the flow rate ratio of the shell (e.g., PEG-rich phase) and core (e.g., dextran-rich phase) from 4:1 to 1:1 to 1:5 resulted in an increase in the size of the core as shown by optical imaging.

A key advantage is that the presence of the two immiscible aqueous phases means that the two phases can have different concentrations of the active ingredients to be encapsulated. A ratio of the concentration of the active ingredient in one aqueous phase to that in the other aqueous phase is defined as a partition coefficient. As long as the partition coefficient is not one, concentration is expected to be different in the two aqueous phases. This can be used for maintaining a concentration gradient between the two phases, which would be impossible if both aqueous phases are miscible, as mixing between the two phases would be faster. Even for species that can diffuse across the interface, the presence of the interface acts as a barrier against such diffusion; this helps to keep leaky active ingredients within the desired phase for longer.

The emulsions described herein exhibit greater stability than prior art emulsions. For example, the emulsions show little or no aggregation for at least about 14 days, 21, days, 30 days, 45 days, 60 days, 75 days, 90 days, four months, five months, six months, seven months, eight months, nine months, ten months, eleven months, one year or longer.

III. Applications

Many all-aqueous emulsions have ultra-low interfacial tension and relatively large dynamic viscosity; thus, formation of w/w emulsions cannot rely on spontaneous jet breakup in conventional microfluidic design as relied on in the prior art. Successful generation of w/w emulsion in modified device geometries is limited to ATPSs with interfacial tension higher than 0.1 mN/m and dynamic viscosity lower than 102 mPa·s, such as the dextran/PEG system and the PEG/salt system. In ATPS containing a protein-rich phase or other polyelectrolyte phases, breakup of the w/w jet is usually restricted by ultra-low interfacial tension and high viscosities of the ATPS, even when using hydrodynamic perturbations.

The all-aqueous electrospray method described herein represents a promising approach in this area. The high voltage applied provides a strong pulling on the viscous jet and the large surface tension induces breakup of the jet which is suitable for emulsions having a high viscosity (>100 mPa·s) and ultra-low interfacial tension. However, ATPS systems with interfacial tension higher than $10^{-4}$ N/m and dynamic viscosity of less than 102 mPa·s have not been studied. Such ATPSs have been found in systems composed of inorganic salts, but the concentrated salt in the solution phases are often too harsh an environment for proteins and cells, partly due to the inevitably high osmolarity. ATPS composed of biocompatible macromolecules are promising alternatives for encapsulation of such materials. Molecular structures of incompatible solutes can be custom-designed, with special considerations on the intermolecular forces and their conformations at the w/w interface in order to tune the system to the materials to be encapsulated.

A. Materials Fabrication

While the fabrication of multi-functional materials can be templated from emulsions with complex structures, the concept has not been sufficiently adapted to the all-aqueous systems. In the sub-micron size range, self-assembly of macromolecules and particles in the ATPS is affected by their interaction with the surrounding molecules. These interactions can be manipulated to control the conformation of biomolecules in all-aqueous multiphase systems, and guide the assembly of copolymers, macromolecules and colloids into desired aggregates.

In the size range of micrometers or higher, generation of multiple all-aqueous emulsions with flexible structures and dimensions provides versatility needed in designing multi-functional materials, such as drug delivery vehicles, biosensors, microreactors and micro-containers. Stacking of emulsions and emulsion-templated materials in large scale will result in highly organized hierarchical structures, including microfibers, membrane and porous scaffolds. Successful construction of these structures is a prerequisite towards functional replication in artificial materials, such as tissue-like scaffolds and photonic materials. Hierarchical assembly of materials can be guided by either all-aqueous phases or their interface. In the assembly of functional biomimetic units, droplet networks can be constructed through 3-D printing and droplet-packing in chambers. Meanwhile, hierarchical assembly of nano-particles has been investigated at the interfaces of two miscible aqueous phases. When this concept is applied to immiscible aqueous phases, assembly of nano-particles can be confined at the w/w interface without extension into bulk aqueous phases.

B. Modeling of Biological Organelles

Aqueous two-phase systems create an excellent all-aqueous environment for the mimicking of cytoplasmic environments in cells. During the differentiation of a single-cell embryo, RNA-binding proteins are found to localize themselves by partitioning; thus, aqueous phase separation may have played an important role in the structuring and assembly of biological components. Biomolecules selectively partition into different aqueous phases, and this selectivity can be enhanced in the presence of protein ligands or enzymes. The partition of biomolecules in the ATPS increases their local concentrations; thus biochemical reactions and molecular assembly are accelerated.

Transfer of biomolecules among the different chambers formed by aqueous phases could be regulated by a semi-permeable membrane, which allows a steady and dynamic microenvironment for cellular metabolism. Compartmentalization of different biomolecules and biological organelles in all-aqueous emulsion-templated vesicles represents a new route to achieve the cyto-mimetic compartments. This provides opportunities to investigate the activities of biomolecules and biological organelles, as well as their synergetic interactions. Once the artificial cyto-mimetic compartments are developed, synthesis of proteins and DNA can be carried out in the physiological microenvironment, where the molecular structure and biological functions of these biomolecules are best preserved.

C. Drug Delivery

The emulsions described here can be used to deliver one or more therapeutic, prophylactic, and/or diagnostic agent and/or cells to a patient in need thereof. As discussed above, the emulsions described therein do not contain an organic solvent and therefore are desirable for encapsulating biomolecules (proteins, nucleic acids, etc.) and/or cells, which can be adversely affected by the presence of organic solvents. Moreover, the presence of a membrane formed by the oppositely charged macromolecules improves the stability of the emulsions allowing them to be prepared and stored for a period of time before use.

The emulsions can be formulated for a variety of routes of administration. In some embodiments, the emulsion is administered enterally (e.g., oral) or parenterally.

"Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

The emulsions can be administered neat, i.e., without additional carriers/excipients. Alternatively, the emulsions can be combined with one or more carriers and/or excipients to prepare a pharmaceutical composition.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers. Water soluble polymers are often used in formulations for parenteral administration. Suitable water-soluble polymers include, but are not limited to, polyvinylpyrrolidone, dextran, carboxymethylcellulose, and polyethylene glycol.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

EXAMPLES

Example 1

Preparation of All Aqueous Emulsions Using Electrostatic Effects

Figure 2:
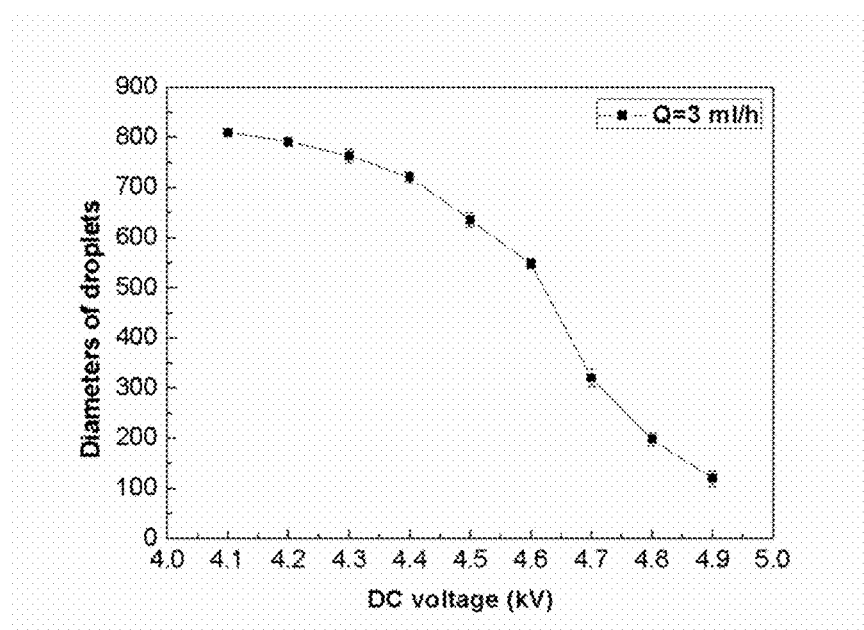
FIG. 2 is a graph showing the diameter of PEG-droplets (microns) as a function of the applied DC voltage (kV).

A dispersed phase of 8 wt % PEG (Mw=8,000) solution charged with a high DC voltage is sprayed into its immiscible aqueous phase of 15 wt % dextran (Mw=500,000) solution through air. The large surface tension between the dispersed phase and air helps to break up the jet quickly into droplets (FIG. 1, panel a). A dripping to jetting transition is observed upon an increase in the applied voltage. In the dripping regime, the charged jet immediately breaks up at the end of the spraying nozzle, yielding monodisperse droplets with a polydispersity of less than 5% (FIG. 1, panels b and c), e.g. By increasing the applied electrical field from 2.1 kV/cm to 2.5 kV/cm, the diameter of the produced droplets is significantly reduced from 810 μm to 120 μm (FIG. 2). In this case, the distance between the positively charged nozzle and the negatively charged electrode ring is 2 cm, and the diameter of the nozzle is 40 micrometers. Further increase in the strength of the electric field leads to polydisperse droplets with smaller sizes. A reduction in the size of the spraying nozzle can produce monodisperse droplets with smaller sizes, e.g. when the size of nozzle is decreased to 20 μm. Uniform droplets with diameters of less than 50 μm can be produced.

Example 2

Preparation of Core-shell all Aqueous Emulsions Using Electrostatic Effects

Two immiscible aqueous phases of 10% dextran (Mw=500,000) and 8 wt % PEG (Mw=8,000) solutions were separately injected into inner and outer glass capillaries, forming a dextran-in-PEG jet (FIG. 1, panel a). The PEG-rich phase was charged by a high-voltage power supply and the compound jet was forced to go through a ring-shaped counter electrode under electrostatic forces. Upon breakup of the jet, core-shell structured droplets fell into the continuous phase of a dextran solution or on the surface of a solid substrate (FIG. 1, panel c). The diameter of the core was varied by varying the flow rate ratio of the PEG-rich (shell) and dextran-rich (core) phase. As the ratio was varied from 4:1 to 1:1 to 1:5, the diameter of the core increased.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for preparing a stabilized all-aqueous emulsion, the method comprising contacting an electrically charged first aqueous phase containing a first solute and one or more charged surfactants with an optionally charged second aqueous phase containing a second solute and one or more charged surfactants which has a charge opposite to the charge of the surfactant in the first aqueous phase, wherein the solutes are incompatible and induce formation of droplets of a dispersed phase in a continuous phase wherein the first aqueous phase and second aqueous phase are contacted using electrospraying.

2. The method of claim 1, wherein the emulsion has a dynamic viscosity of >100 mPa·s or an interfacial tension of <0.1 mN/m.

3. The method of claim 1, wherein the first and second solutes are selected from the group consisting of polyethylene glycol (PEG), dextran, methyl cellulose, sodium dextran sulfate, polyvinyl alcohol (PVA), polyvinyl pyrrolidone (PVP); tripotassium phosphate, sodium citrate, sodium sulfate, and disodium phosphate.

4. The method of claim 3, wherein the first solute is PEG and the second solute is dextran.

5. The method of claim 4, wherein the molecular weight of PEG is about 8,000-20,000 Daltons and the concentration of PEG is 8% and the molecular weight of dextran is about 500,000 Daltons and the concentration of dextran is about 5-15%.

6. The method of claim 1, wherein the first aqueous phase and/or the second aqueous phase further contains one or more therapeutic, prophylactic, and/or diagnostic agents that are encapsulated in the droplets of the dispersed phase.

7. The method of claim 1, wherein the first aqueous phase and/or the second aqueous phase further contains cells that are encapsulated in the droplets of the dispersed phase.

8. An emulsion prepared by the method of claim 1.

9. The emulsion of claim 8, wherein the droplets comprise a membrane on the surface of the droplets which prevents coalescence of the droplets and/or prevent leakage of the contents of the droplets.

10. The emulsion of claim 9, wherein the diameter of the droplets is from about 100 microns to about 1000 microns.

11. A pharmaceutical composition comprising the emulsion of claim 8 and one or more pharmaceutically acceptable carriers.

12. A method for administering one or more therapeutic, prophylactic, and/or diagnostic agent to a patient in need thereof, the method comprising administering the emulsion of claim 8.

13. The method of claim 12, wherein the agent is a biomolecule, a small molecule, or combinations thereof.

14. The method of claim 12, wherein the emulsion is administered orally.

15. The method of claim 12, wherein the emulsion is administered parenterally.

16. A method for administering cells to a patient in need thereof, the method comprising administering the emulsion of claim 8.

17. The method of claim 16, wherein the emulsion is administered parenterally.

* * * * *